United States Patent
Alarcon et al.

(10) Patent No.: US 11,801,353 B2
(45) Date of Patent: Oct. 31, 2023

(54) ELECTRONIC CIGARETTE WITH ILLUMINATED TIP

(71) Applicant: Fontem Holdings 1 B.V., Amsterdam (NL)

(72) Inventors: Ramon Alarcon, Los Gatos, CA (US); Adam Hoffman, Campbell, CA (US); Christopher Myles, San Jose, CA (US); James R. Conrey, San Jose, CA (US)

(73) Assignee: Fontem Ventures B.V., Amsterdam (NL)

( * ) Notice: Subject to any disclaimer, the term of this patent is extended or adjusted under 35 U.S.C. 154(b) by 0 days.

(21) Appl. No.: 16/950,883

(22) Filed: Nov. 17, 2020

(65) Prior Publication Data

US 2021/0170121 A1   Jun. 10, 2021

Related U.S. Application Data

(60) Continuation of application No. 16/175,129, filed on Oct. 30, 2018, now Pat. No. 10,863,776, which is a
(Continued)

(51) Int. Cl.
*A61M 15/06* (2006.01)
*A61M 11/04* (2006.01)
(Continued)

(52) U.S. Cl.
CPC ............ *A61M 15/06* (2013.01); *A24F 40/40* (2020.01); *A24F 40/50* (2020.01); *A24F 40/60* (2020.01); *A61M 11/042* (2014.02); *F21V 23/0442* (2013.01); *F21V 33/0004* (2013.01);
*G02B 6/0036* (2013.01); *G02B 6/0051* (2013.01); *G02B 6/0068* (2013.01);
(Continued)

(58) Field of Classification Search
CPC ................ A61M 15/06; A61M 11/042; A61M 2016/0021; A61M 2205/3331; A61M 2205/3368; A61M 2205/3653; A61M 2205/583; A61M 2205/8206; A24F 40/50; A24F 40/60; A24F 40/40; A24F 40/10; H05B 45/10; F21V 23/0442; F21V 33/0004; G02B 6/0036; G02B 6/0051; G02B 6/0068; G02B 6/0083; F21Y 2115/10; F21W 2111/10
See application file for complete search history.

(56) References Cited

U.S. PATENT DOCUMENTS 2,055,217 A   9/1936   Gauthier
2,849,585 A   8/1958   Evans
(Continued)

FOREIGN PATENT DOCUMENTS

CA   2731485     8/2012
CN   2870485 Y   2/2007
(Continued)

*Primary Examiner* — Truc T Nguyen
(74) *Attorney, Agent, or Firm* — Dykema Gossett PLLC

(57) ABSTRACT

Aspects of the instant disclosure relate to electronic cigarettes. More particularly, to electronic cigarettes including a circumferential light guide that distributes light transmitted by a light source, and controller circuitry that variably illuminates the circumferential light guide of the electronic cigarette based on a user's draw strength.

15 Claims, 9 Drawing Sheets

Related U.S. Application Data continuation of application No. 15/901,328, filed on Feb. 21, 2018, now Pat. No. 10,143,241, which is a division of application No. 15/219,043, filed on Jul. 25, 2016, now Pat. No. 9,974,338.

(51) Int. Cl.

| | | |
|---|---|---|
| *H05B 45/10* | (2020.01) | |
| *A24F 40/40* | (2020.01) | |
| *A24F 40/50* | (2020.01) | |
| *A24F 40/60* | (2020.01) | |
| *F21V 23/04* | (2006.01) | |
| *F21V 33/00* | (2006.01) | |
| *F21V 8/00* | (2006.01) | |
| *A61M 16/00* | (2006.01) | |
| *A24F 40/10* | (2020.01) | |
| *F21Y 115/10* | (2016.01) | |
| *F21W 111/10* | (2006.01) | |

(52) U.S. Cl.
CPC .......... *G02B 6/0083* (2013.01); *H05B 45/10* (2020.01); *A24F 40/10* (2020.01); *A61M 2016/0021* (2013.01); *A61M 2205/3331* (2013.01); *A61M 2205/3368* (2013.01); *A61M 2205/3653* (2013.01); *A61M 2205/583* (2013.01); *A61M 2205/8206* (2013.01); *F21W 2111/10* (2013.01); *F21Y 2115/10* (2016.08)

(56) References Cited

U.S. PATENT DOCUMENTS

| | | | |
|---|---|---|---|
| 3,334,636 | A | 8/1967 | Zuber |
| 6,407,807 | B1 | 6/2002 | Focke |
| 8,539,959 | B1 | 9/2013 | Scatterday |
| 8,550,069 | B2 | 10/2013 | Alelov |
| 8,714,150 | B2 | 5/2014 | Alelov |
| 8,757,147 | B2 | 6/2014 | Terry et al. |
| 8,851,068 | B2 | 10/2014 | Cohen |
| 8,899,239 | B2 | 12/2014 | Hon |
| 8,931,492 | B2 | 1/2015 | Scatterday |
| 8,975,764 | B1 | 3/2015 | Abehasera |
| 9,095,174 | B2 | 8/2015 | Capuano |
| D822,273 | S | 7/2018 | Bagai |
| 10,349,676 | B2 | 7/2019 | King et al. |
| 2005/0016550 | A1 | 1/2005 | Katase |
| 2013/0192615 | A1 | 8/2013 | Tucker et al. |
| 2013/0228191 | A1 | 9/2013 | Newton |
| 2013/0298905 | A1 | 11/2013 | Levin et al. |
| 2013/0333712 | A1 | 12/2013 | Scatterday |
| 2014/0053856 | A1 | 2/2014 | Liu |
| 2014/0069444 | A1 | 3/2014 | Cypher et al. |
| 2014/0083442 | A1 | 3/2014 | Scatterday |
| 2014/0096782 | A1 | 4/2014 | Ampolini et al. |
| 2014/0174459 | A1 | 6/2014 | Burstyn |
| 2014/0261488 | A1 | 9/2014 | Tucker |
| 2014/0290675 | A1 | 10/2014 | Xiang |
| 2015/0000683 | A1 | 1/2015 | Liu |
| 2015/0020830 | A1 | 1/2015 | Koller |
| 2015/0047658 | A1 | 2/2015 | Cyphert et al. |
| 2015/0047661 | A1 | 2/2015 | Blackley et al. |
| 2015/0053214 | A1 | 2/2015 | Alarcon |
| 2015/0157054 | A1 | 6/2015 | Liu |
| 2015/0181941 | A1 | 7/2015 | Liu |
| 2015/0181945 | A1 | 7/2015 | Tremblay |
| 2015/0200385 | A1 | 7/2015 | Liu |
| 2015/0208726 | A1 | 7/2015 | Liu |
| 2015/0216233 | A1 | 8/2015 | Sears et al. |
| 2015/0296888 | A1 | 10/2015 | Liu |
| 2015/0305409 | A1 | 10/2015 | Verleur et al. |
| 2015/0351456 | A1 | 12/2015 | Johnson et al. |
| 2016/0021929 | A1 | 1/2016 | Sawalha |
| 2016/0032702 | A1 | 2/2016 | Gay |
| 2016/0073690 | A1 | 3/2016 | Liu |
| 2016/0106154 | A1 | 4/2016 | Lord |
| 2016/0192705 | A1 | 7/2016 | Borkovec |
| 2016/0262450 | A1 | 9/2016 | Liu |
| 2017/0006916 | A1 | 12/2017 | Liu |
| 2018/0020725 | A1* | 1/2018 | Alarcon ............... G02B 6/0036 131/329 |
| 2018/0020727 | A1 | 1/2018 | Hoffman |
| 2020/0359691 | A1* | 11/2020 | Lindars ................. A24F 40/465 |
| 2021/0059305 | A1* | 3/2021 | Clough .................. A24F 40/40 |

FOREIGN PATENT DOCUMENTS

| | | |
|---|---|---|
| CN | 203575650 U | 5/2014 |
| CN | 104811633 A | 7/2015 |
| WO | 2013040814 A1 | 3/2013 |
| WO | 2013148810 A1 | 10/2013 |
| WO | 2014144678 A2 | 9/2014 |
| WO | 2014205811 A1 | 12/2014 |
| WO | 2015035510 A1 | 3/2015 |
| WO | 2015077645 A1 | 5/2015 |
| WO | 2015107552 A1 | 7/2015 |
| WO | 2016010864 A1 | 1/2016 |

* cited by examiner

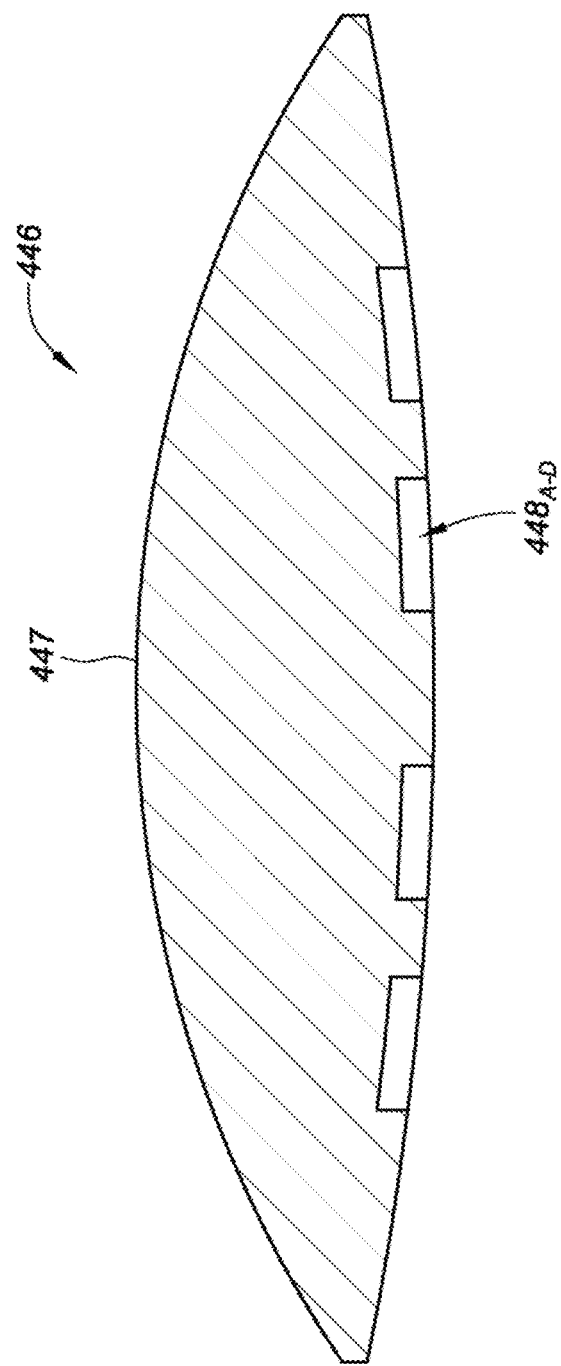

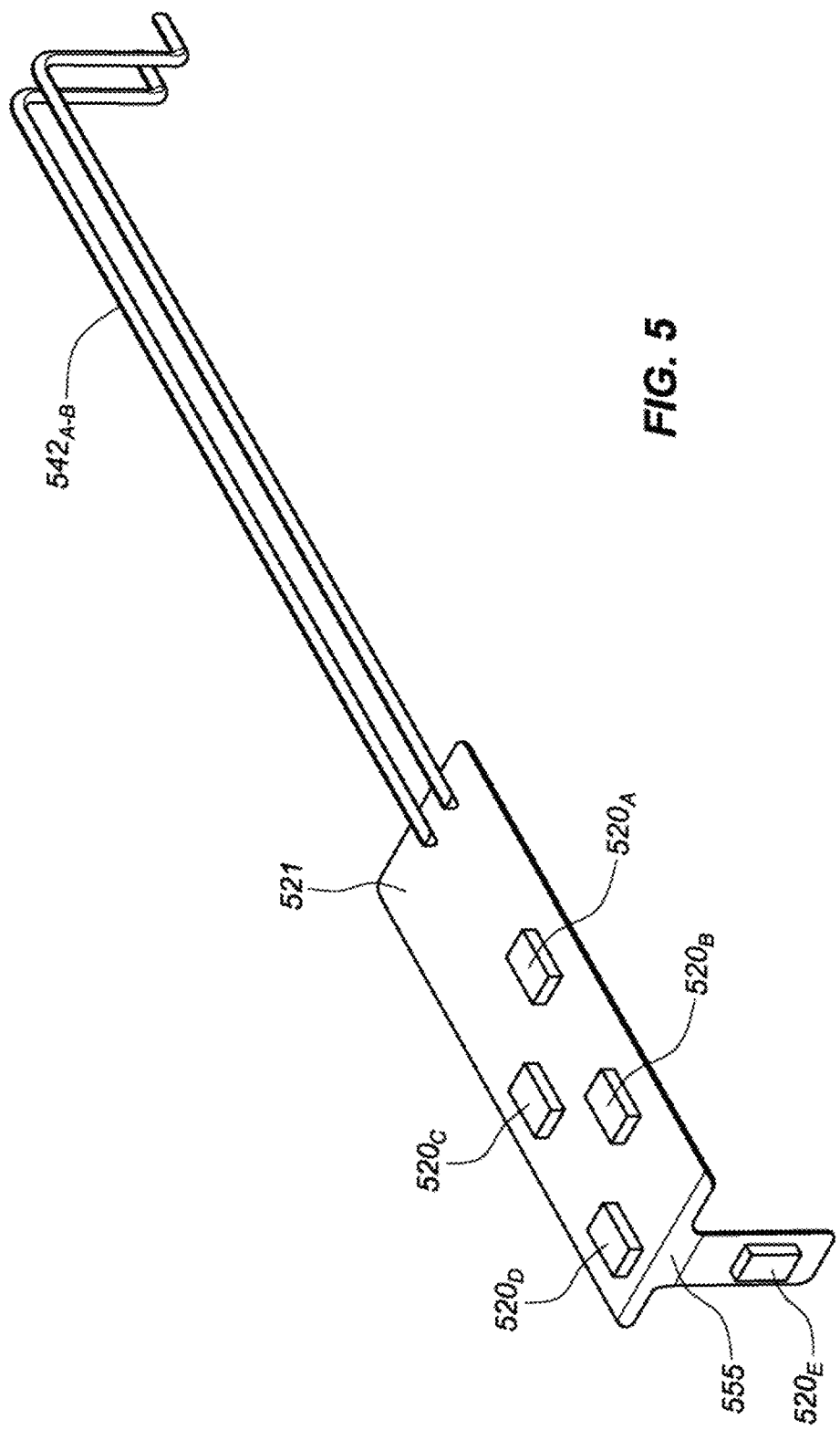

ELECTRONIC CIGARETTE WITH ILLUMINATED TIP

CROSS-REFERENCE TO RELATED APPLICATIONS

This application is a continuation of application Ser. No. 16/175,129, filed 30 Oct. 2018, which is a continuation of application Ser. No. 15/901,328, filed 21 Feb. 2018, which is a divisional of application Ser. No. 15/219,043, filed 25 Jul. 2016, the entire contents of which are herein incorporated by reference.

BACKGROUND a. Field

The instant disclosure relates to an electronic cigarette with an illuminated tip; and more particularly to structure and controller circuitry that illuminates the tip of the electronic cigarette based on draw strength.

b. Background Art

Electronic cigarettes, also known as e-cigarette (eCigs) and personal vaporizers (PVs), are electronic inhalers that vaporize or atomize a liquid solution into an aerosol mist that may then be delivered to a user. A typical eCig has two main parts—a power supply portion and a cartomizer (also referred to as an atomizer/liquid reservoir portion). The power supply portion typically includes a rechargeable lithium-ion (Li-ion) battery, a light emitting diode (LED), and a pressure sensor. The cartomizer typically includes a liquid solution, an atomizer and a mouthpiece. The atomizer typically includes a heating coil that vaporizes the liquid solution.

The foregoing discussion is intended only to illustrate the present field and should not be taken as a disavowal of claim scope.

BRIEF SUMMARY

In one embodiment of the present disclosure, an eCig is disclosed. The eCig including a circumferential light guide that seeks to evenly distribute light transmitted by a light source, and controller circuitry that illuminates the circumferential light guide of the electronic cigarette based on a user's draw strength.

Embodiments of the present disclosure are directed to an electronic cigarette including a sensor, controller circuitry, and a light source. The sensor determining a user draw characteristic, and transmitting a draw signal indicative of the determined user draw characteristic. The controller circuitry communicatively coupled to the sensor, and receives the draw signal from which it determines a light intensity signal transmission. The light source is communicatively coupled to the controller circuitry, and receives the light intensity signal from the sensor—thereafter emitting an intensity of light corresponding to the received light intensity signal. In some embodiments, the user draw characteristic comprises a magnitude of a user draw on the electronic cigarette. In more specific embodiments, the sensor comprises a mass airflow sensor, wherein the user draw characteristic corresponds to a mass of air moving through the electronic cigarette during the user draw.

Various embodiments of the present disclosure are directed to an electronic cigarette including a sensor, a light source, and controller circuitry. The sensor determines a magnitude of a draw characteristic, and transmits a signal indicative of the determined magnitude of the draw characteristic. The light source emits a varying intensity of light in response to an input signal. The controller circuitry is communicatively coupled to the sensor and the light source, and the controller circuitry receives, from the sensor, the signal indicative of a draw characteristic. In response to receiving the signal indicative of the determined magnitude of the draw characteristic, the controller circuitry associates the determined magnitude of the draw characteristic with an intensity of the light source, and generates the input signal to the light source based on the light intensity associated with the determined magnitude of the draw characteristic. In some embodiments, the sensor is a mass airflow sensor that determines a mass flowrate of the draw.

Some embodiments of the present disclosure are directed to a circumferential light guide apparatus including a partial circumferential feature, opposing distal ends on either side of the partial circumferential feature, an aperture between the distal ends, and an outer surface. The opposing distal ends receive and direct light into the partial circumferential feature. In response to receiving light, the outer surface including variable surface texture distributes the directed light along the outer surface of the circumferential light guide. In some embodiments, the circumferential light guide apparatus further includes an electronic circuit board positioned within the aperture. The electronic circuit board including at least one light source substantially directed toward at least one of the opposing distal ends.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

Various example embodiments may be more completely understood in consideration of the following detailed description in connection with the accompanying drawings.

FIG. 4C is a cross-sectional view of the tip diffuser taken along line A-A of FIG. 4A, consistent with various aspects of the present disclosure.

FIG. 5 is an isometric front view of a flexible circuit board, consistent with various aspects of the present disclosure.

Figure 1:
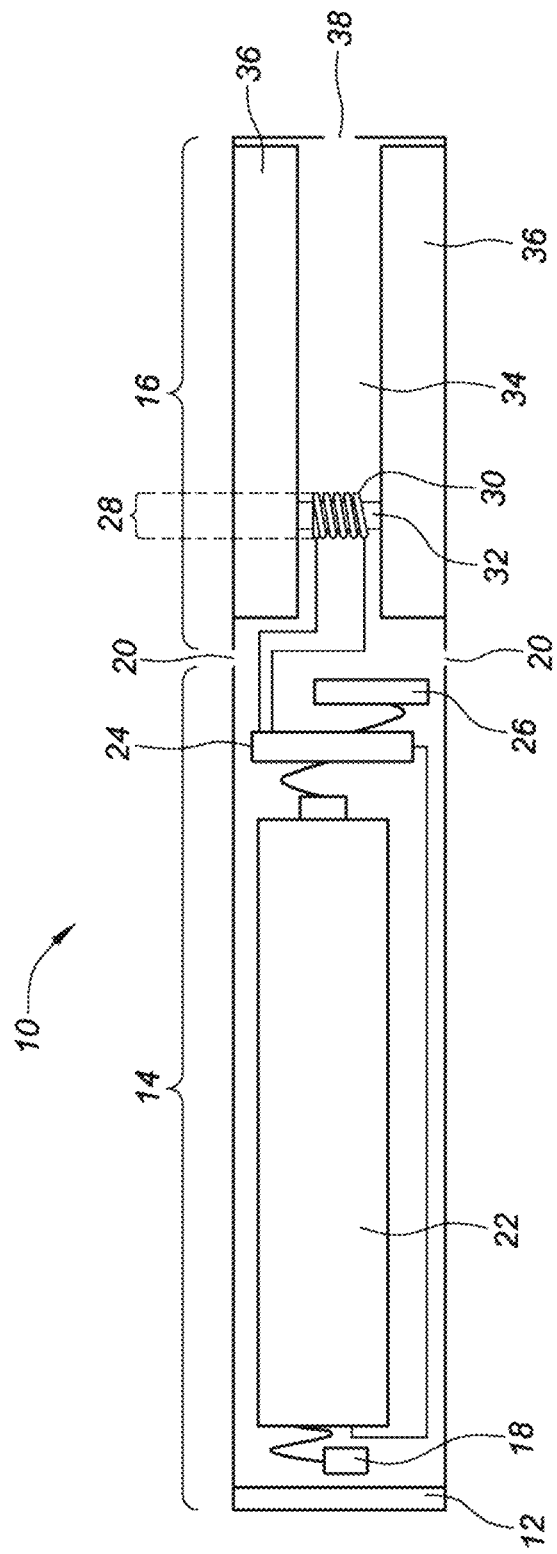
FIG. 1 is a cross-sectional side view of an eCig, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION OF EMBODIMENTS

The disclosure and the various features and advantageous details thereof are explained more fully with reference to the non-limiting embodiments and examples that are described and/or illustrated in the accompanying drawings and detailed in the following.

Throughout the following, an electronic smoking device will be exemplarily described with reference to an e-cigarette. As is shown in FIG. 1, an e-cigarette 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2:
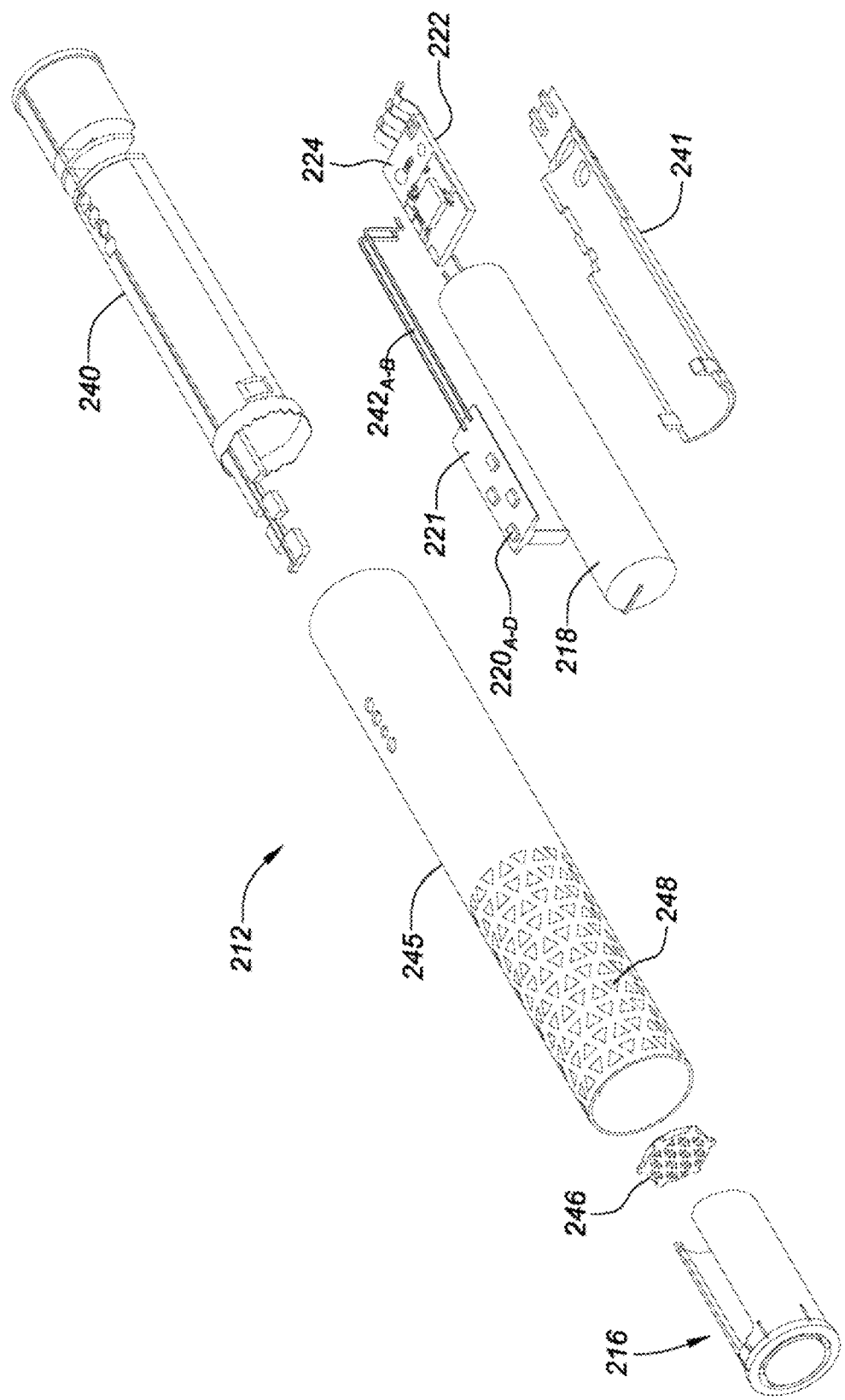
FIG. 2 is a partial exploded assembly view of an eCig, consistent with various aspects of the present disclosure.

FIG. 2 is a partial exploded assembly view of an eCig power supply portion 212, consistent with various aspects of the present disclosure. The power supply portion 212 houses a number of electrical components that facilitate the re-charging and re-use of the power supply portion 212 with disposable and refillable atomizer/liquid reservoir portions (14 as shown in FIG. 1), which are also referred to as cartomizers. A battery 218 is electrically coupled to controller circuitry 222 on a printed circuit board. A sensor 224 for determining one or more characteristics of a user's draw from the eCig is also located on the printed circuit board, and communicatively coupled to the controller circuitry 222. In various embodiments consistent with the present disclosure, the sensor 224 may be a mass air-flow sensor, a pressure sensor, a velocity sensor, a heater coil temperature sensor, or any other sensor that may capture relevant draw characteristics (either directly or through indirect correlations). In the present embodiment, the sensor 224 is a mass air-flow sensor that determines the flow of air across the sensor 224 on the surface of the printed circuit board. The measured flow of air is then drawn through the cartomizer 14 and into a user's mouth. By measuring the mass flow rate of air through the power supply portion 212, the controller circuitry 222 may adjust a heating profile of a heating coil in a cartomizer (e.g., power, length of time, etc.), as well as provide a variable visual indication of the strength of the draw—by way of LEDs $220_{A-D}$ which may be independently addressed by the controller circuitry or powered at varying intensities to indicate characteristics of the eCig's functionality. For example, varying the illumination intensity based on the sensed mass air-flow. In further embodiments, the LEDs may also indicate other functional aspects of the eCig, such as remaining battery life, charging, sleep mode, among others. In various embodiments of the present disclosure, a draw characteristic may be the length of a draw, volume of a draw, mass of air moving through the eCig during the draw, velocity of air during the draw, the change over time of one or more of the above draw characteristics, cut-off and/or thresholds associated with one or more of the above draw characteristics, time to peak of a draw characteristic, among others readily measurable characteristics.

In various embodiments of the present disclosure, electrical pins extending from the printed circuit board may be electrically coupled to a cartomizer, and thereby allow for both energy transfer and data communication between the power supply portion 212 and cartomizer (not shown). In various other embodiments, pins may extend from a surface of the printed circuit board to an exterior of the power supply portion to facilitate charging and data communication with external circuitry.

To provide user indications of status, power remaining, use, error messages, among other relevant information, a flexible printed circuit board 221 is communicatively coupled to controller circuitry 222 via wire leads $242_{A-B}$. The flexible circuit board 221 may include one or more light sources. In the present embodiment, the flexible circuit board 221 includes LEDs $220_{A-E}$. When assembled into the rest of the power supply portion 212, the light emitting diodes $220_{A-D}$ both illuminate a circumferential portion of light guide 216 and a tip diffuser 246 that thereby illuminates a distal end of the light guide 216. The tip diffuser 246 and the light guide 216 together facilitate even illumination of the distal end of the power supply portion 212 in response to the activation of the LEDs $220_{A-D}$. In other embodiments, the flexible circuit board 221 may not require an LED substantially directed at the tip diffuser 246; for example, where the light guide 216 directs light from the LEDs $220_{A-D}$ through the tip diffuser 246 and thereby illuminates the distal end of the light guide.

As shown in FIG. 2, once electrically coupled to one another (e.g., by solder), battery 218, flexible printed circuit board 221, and a printed circuit board containing controller circuitry 222 and sensor 224 are encased by upper sub-assembly housing 240 and lower sub-assembly housing 241. The upper and lower sub-assembly housing portions positively locate the various components with the sub-assembly. In many embodiments, upper and lower sub-assembly housing portions utilize locating pins and integral locking features (e.g., snap features) to maintain the sub-assembly after assembly.

Once assembly is complete on the sub-assembly, the sub-assembly may be slid into tube 245 from one end and tip diffuser 246 and circumferential light guide 216 may be inserted from the opposite end of the tube to complete assembly of power supply portion 212. By way of the distal tip of the circumferential light guide 216 and translucent portion 248 in tube 245, light emitting diodes $220_{A-D}$ may illuminate evenly around a distal circumferential portion of the tube 245, and a distal tip.

In various embodiments of the present disclosure, translucent portion 248 on tube 245 may include various different patterns, shapes, images and/or logos. In the present embodiment, the translucent portion 248 is a plurality of triangles. The translucent portion 248 may be laser etched on to a painted surface of the tube 245, silk screened, drilled or otherwise cut into an outer surface of the tube 245, and/or the tube itself can be (semi-)translucent and the pattern may be disposed on an outer surface of circumferential light guide 216.

Figure 3A:
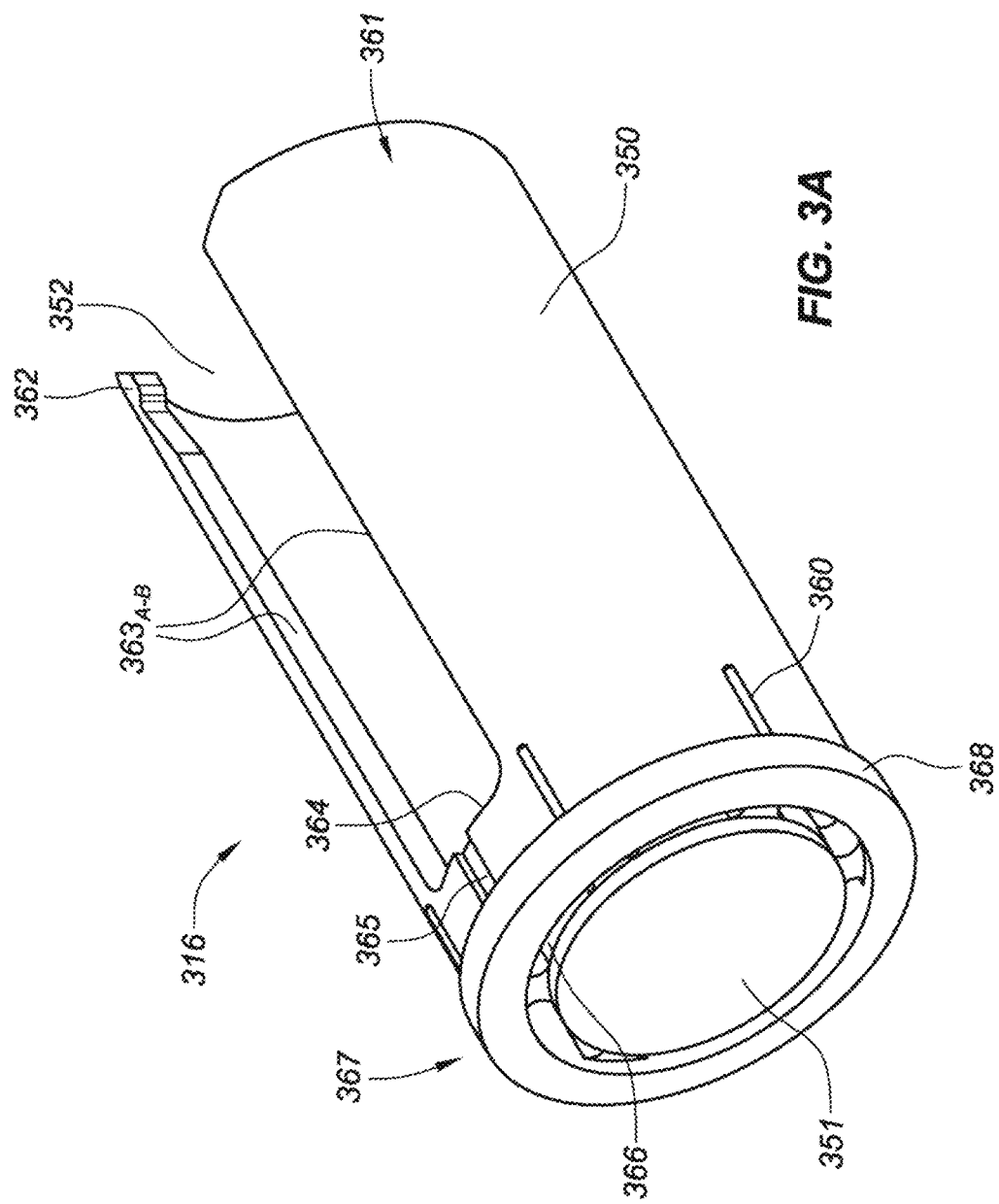
FIG. 3A is an isometric front view of a circumferential light guide, consistent with various aspects of the present disclosure.

FIG. 3A is an isometric front view of a circumferential light guide 316, consistent with various aspects of the present disclosure. As shown in FIG. 3A, a circuit board receiving slot 352 forms distal ends of the circumferential light guide 316. When assembled, LEDs are located within the circuit board receiving slot 352 and faced to illuminate the distal ends of the circumferential light guide, as well as distal outer surface 351. The light then travels from the distal ends of the circumferential portion within the circumferential light guide and evenly diffuses out from outer surface 350 in response to a variable surface texture on the outer surface that accounts for the location of the LEDs in the circuit board receiving slot 352, as well as the illumination patterns of each of the LEDs. One exemplary implementation of variable surface texture is shown in relation to FIGS. 3B-D.

A circuit board including LEDs is inserted into a circuit board receiving slot 352 of circumferential light guide 316, which is bound by longitudinally-extending slot walls 363A-B and circumferentially-extending slot wall 364. The slot walls 363 and 364 receive light from LEDs on-board the circuit board and distributes the light throughout a partial circumferential feature 361 and end cap feature 367.

During installation of a circumferential light guide 316 into a power supply portion, an alignment grove 365 aligns with a corresponding feature on a tube 245, and prevents the circumferential light guide from spinning within the tube. Once the circumferential light guide 316 is inserted into the tube 245, a retention tooth 362 at a distal end of the circumferential light guide couples to a mating portion on an upper sub-assembly housing 240 (as shown in FIG. 2); which in conjunction with friction ribs 360 which are press fit against the tube 240 and light guide positioning ring 368—the circumferential light guide 316 is properly located within the tube 245 and coupled therein. The light guide positioning ring 368 defining a proximal facing annular surface that seats against a distal end of the tube 245 in the assembled power supply portion 212.

One or more air inlet channels 366 in a distal outer surface 351 of an end cap feature 367 may provide air inlets to facilitate the flow of air through power supply portion 212; for example, where a user draws on an air inlet 38 of the atomizer/liquid reservoir portion 16.

Figure 3D:
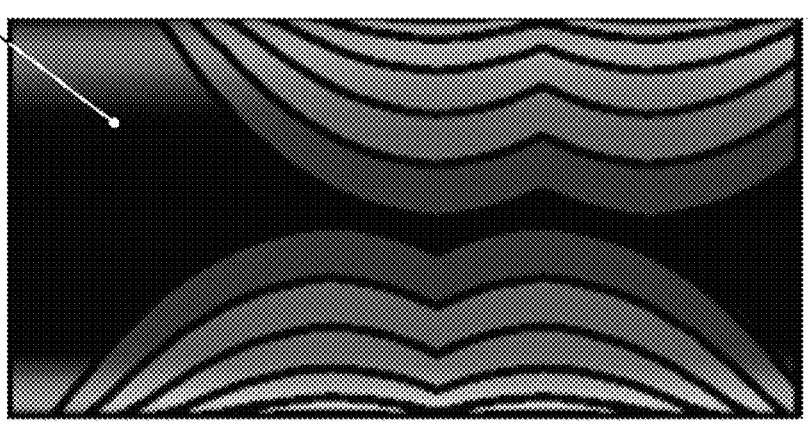
FIG. 3D is a bottom view of a circumferential light guide, consistent with various aspects of the present disclosure.
Figure 3C:
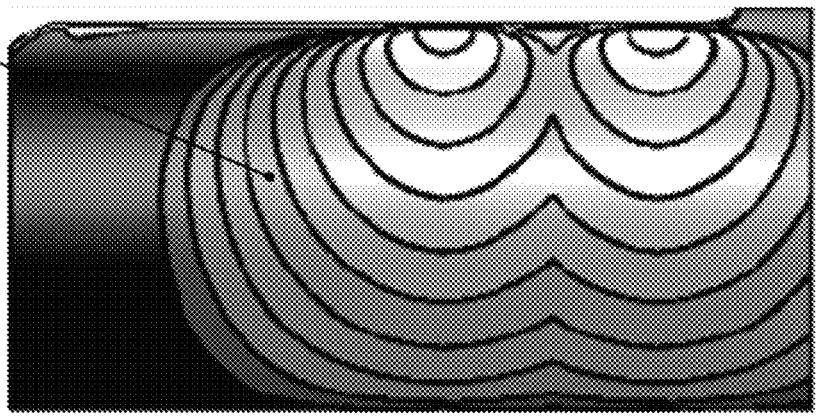
FIG. 3C is a side view of a circumferential light guide, consistent with various aspects of the present disclosure.
Figure 3B:
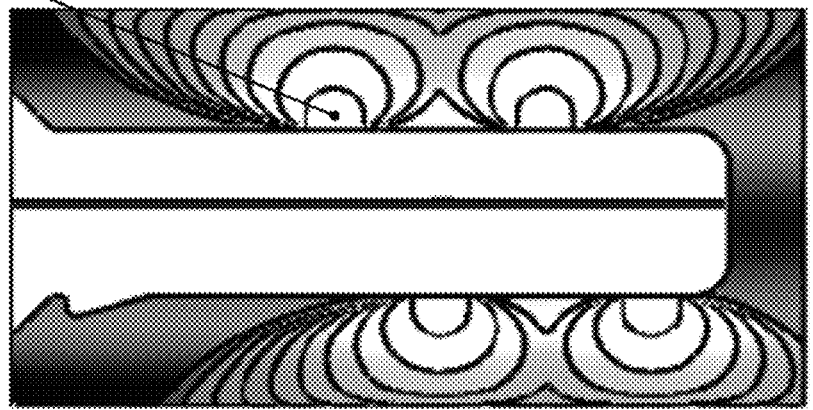
FIG. 3B is a top view of a circumferential light guide, consistent with various aspects of the present disclosure.

FIG. 3B is a top view, FIG. 3C is a side view, and FIG. 3D is a bottom view of a circumferential light guide 316, as shown in FIG. 3A, consistent with various aspects of the present disclosure. The variable surface texturing of outer surface 350 is indicated by gray-scale—with the lighter surface texturing indicated by the lighter shading 356, intermediate surface texturing indicated by the medium shading 357, and the heaviest surface texturing indicated by the darkest shading 358. Accordingly, in areas near an LED where illumination is the greatest, texturing on the outer surface 350 is the lowest as additional diffusion is not necessary. However, the farther away and/or off-center from the LED, the less illumination that reaches a given location along the circumferential light guide 316—necessitating additional texturing to improve diffusion of light at that location. By implementing the surface texturing shown in FIGS. 3B-D, uneven illumination may be compensated for by the surface texture of the light guide to substantially produce even illumination of the light guide around a circumference and length thereof.

Figure 4A:
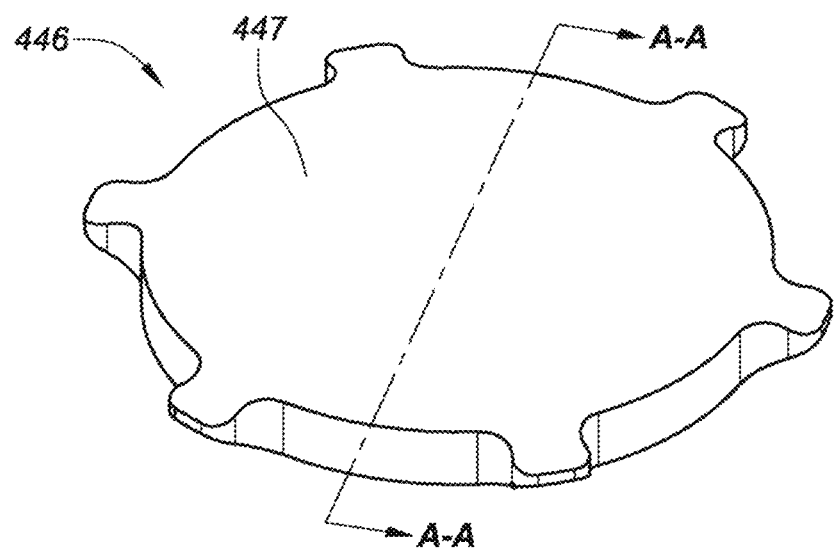
FIG. 4A is an isometric front view of a tip diffuser, consistent with various aspects of the present disclosure.

FIG. 4A is an isometric front view of a tip diffuser 446, consistent with various aspects of the present disclosure. As shown in FIG. 4A, a front surface of the tip diffuser 446 is shown including a convex lens 447. The tip diffuser 446, when positioned in front of an LED (or other light source), diffuses the received light to produce an even illumination along a distal outer surface 351 of circumferential light guide 316 (as shown in FIG. 3A). In various embodiments, the tip diffuser may include fixation prongs 449 extending from an outer circumference thereof that facilitate localization and/or coupling of the tip diffuser 446 within the circumferential light guide 316 once assembled. Once the tip diffuser 446 is mounted within a circumferential light guide 216 via the fixation prongs 449, the prongs define a series of flow channels for air that traverses past the air inlets 366 (as shown in FIG. 3A).

Figure 4B:
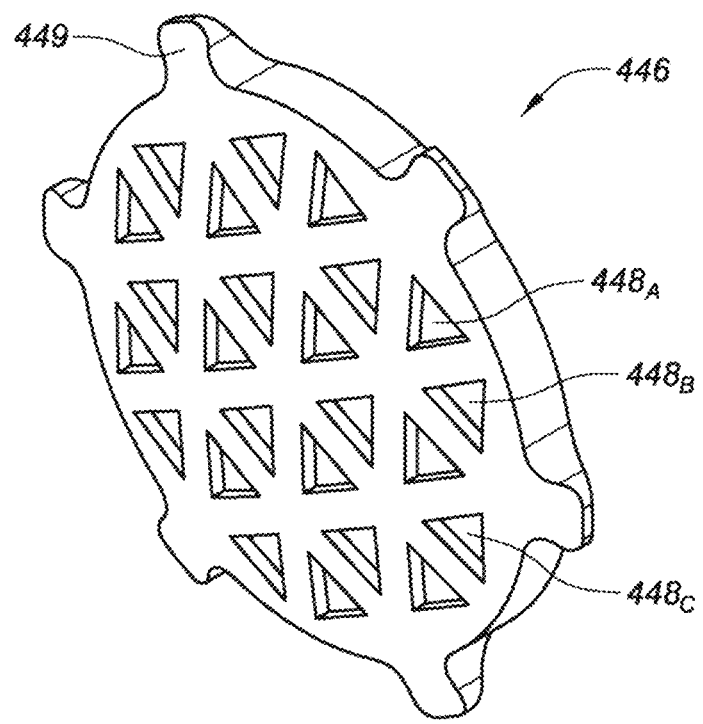
FIG. 4B is an isometric back view of the tip diffuser of FIG. 4A, consistent with various aspects of the present disclosure.

FIG. 4B is an isometric back view of the tip diffuser 446 of FIG. 4A, consistent with various aspects of the present disclosure. The back-side of the tip diffuser 446 includes a plurality of light diffusing features $448_{A-C}$ which together form a pattern. In the present embodiment, the light diffusing features $448_{A-C}$ are triangular shapes cut into a back surface of the tip diffuser 446. When light (e.g., from a single point source) is transmitted toward a back surface of the tip diffuser 446, the light diffusing features $448_{A-C}$ diffuse the light traveling through the tip diffuser 446 to produce an evenly illuminated front surface of the tip diffuser.

In various other embodiments of the present disclosure, the tip diffuser 446 may include various other optical diffusion techniques known to those skilled in the art, including, for example, surface texturing, lensing, and material characteristics or additives to the tip diffuser 446 that facilitate internal light diffusion. In some embodiments of the present disclosure the side-walls of the light diffusing features $448_{A-C}$ are sloped, straight, or rounded to further facilitate diffusion of light through the tip diffuser 446.

The light diffusing features $448_{A-C}$ of FIG. 4 may take various shapes, with varying diffusion characteristics. In some embodiments, the light diffusing features $448_{A-C}$ may be a material additive, such as surface texturing or more defined features. In further embodiments, an array of lensing or other features extending into a back and/or front side of the tip diffuser 446 may also be utilized to achieve desired even light illumination across a front surface of the tip diffuser 446 from a single point light source.

FIG. 4C is an cross-sectional side view of the tip diffuser 446 of FIG. 4A, consistent with various aspects of the present disclosure. As shown in FIG. 4C, the tip diffuser 446 forms a bi-convex lens including a convex lens 447 on a front surface of the tip diffuser, and another convex lens on a back surface, and a plurality of diffusing features $448_{A-C}$ extending into a light receiving surface of the tip diffuser 446. The convex lens and the light diffusing features $448_{A-C}$ on the light receiving surface facilitate consistent illumination of the light transmitting surface. After light travels through the tip diffuser 446, the convex lens 447 on the light transmitting surface distributes the light across a wide viewing angle.

In view of the present example embodiments of tip diffusers, a skilled artisan will readily be capable of developing various other tip diffusers that achieve the same goal of even light illumination across a distal surface of an eCig using various other known light lensing techniques, and without undue experimentation.

FIG. 5 is an isometric front view of a flexible circuit board 521, consistent with various aspects of the present disclosure. As shown in the exploded view of the power supply portion 212, FIG. 2, the flexible circuit board 521 (also referred to as a flex circuit) once assembled straddles a battery 218, with a portion 555 of the flex circuit 521 bent at a right angle relative to the rest of the flex circuit, and wire leads $542_{A-B}$ make another right angle after extending from the flex circuit 521 to fully encompass the battery 218 and to communicatively couple to controller circuitry 222. LEDs $520_{A-D}$ may be side-firing LEDs that illuminate opposing distal ends of circumferential light guide 216 when the flex circuit 521 is positioned within an circuit board receiving slot 352 of the light guide 316 (as shown in FIG. 3A). LED $520_E$ on the folded portion of the flex circuit 521 may be a top-firing LED which illuminates a tip diffuser 446 and a distal outer surface 351 of a circumferential light guide (as shown in FIG. 2). In various embodiments of the present disclosure, the LEDs $520_{A-E}$ may be dependently or independently addressable, and may be powered by amplifiers that facilitate variable illumination output of the LEDs.

In some embodiments of the present disclosure, flex circuit 521 may include various electrical components, besides LEDs $520_{A-E}$, such as driver circuitry for the LEDs 520 (e.g., operational amplifiers), among other components.

LEDs $520_{A-E}$ may be utilized to indicate various statuses, modes, and operational characteristics to the user. For example, during operation, the LEDs $520_{A-E}$ may glow to indicate operation of the eCig (e.g., where the user is taking a draw). In further more specific embodiments, based on an input from a sensor indicative of a user's draw strength, the LEDs $520_{A-E}$ may fluctuate in intensity dependent on the user's draw strength. The relationship between the sensor output and the LED illumination being either a linear or non-linear relationship. In specific embodiments, this relationship may be controlled by a formula such as a transfer function, and more specifically a logarithmic transfer function. Similarly, in embodiments where the LEDs $520_{A-E}$ are independently addressable, based on a sensor input to the controller circuitry, the intensity of each LED may be independently varied in order to create a variable smoldering affect similar to a user taking a draw from a traditional cigarette. In one example embodiment, the LED furthest from the distal tip would lightly flicker when idle between user draws. When a user initiates a draw from the eCig, the brightness and the number of LEDs activated during the draw may be varied based on the sensed strength of the draw and vary over the length of the draw, thereby creating an enhanced user experience.

In further embodiments, one or more of the LEDs $520_{A-E}$ may be multi-color LEDs to facilitate customization of the user experience and/or to further facilitate communication of various states of the eCig such as charging, low battery, operation, sleep mode, among others. As one example embodiment, to indicate battery charging, one or more of the LEDs may ramp up from an off state to full light intensity before ramping back down to an off state, and repeating. When the battery life is low, a heartbeat-type illumination intensity profile may be utilized to indicate low battery life to the user. Similarly, blinks of varying frequency may also be used to indicated messages to the user.

In various implementations of the present disclosure, LEDs may be driven with reduced duty cycles to create the appearance of dimmed lighting.

In specific embodiments of the present disclosure, it can be desirable to maintain a consistent visual appearance to the user throughout a use cycle of a battery. However, as the battery drains over a use cycle, the amount of voltage driving the LEDs is diminished. In such a configuration, the visual appearance (e.g., the brightness) associated with a given visual indication of the eCig changes over the use cycle. To compensate for the battery's varying voltage, controller circuitry 222 periodically measures the battery voltage and compensates for the change in voltage from a full charge by varying the duty cycle of the LEDs. Thereby maintaining a consistent illumination of the LEDs over the use cycle of the battery, for a given visual indication.

After an initial draw from a user, after a period of inactivity, controller circuitry 222 of the eCig may enter a session mode whereby one or more LEDs 520 remain active during a set period of time (e.g., indicative of a typical smoke break, 5 minutes). The length of this session may be indicated by the LEDs 520, which can appear to smolder between draws. After the session length is exceeded, the LEDs are deactivated indicating that the session has ended.

Figure 6A:
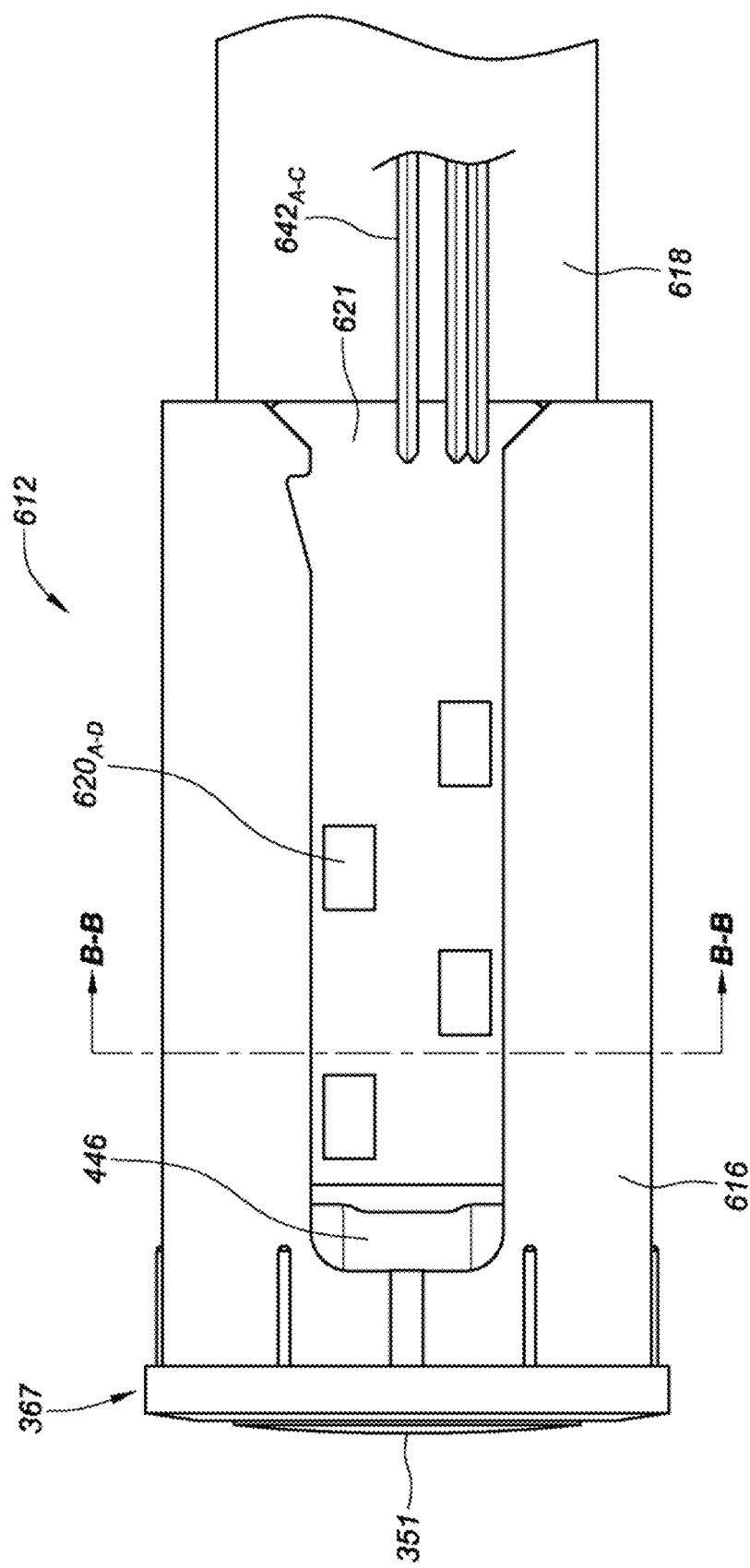
FIG. 6A is a top view of a partially assembled eCig, consistent with various aspects of the present disclosure.

FIG. 6A is a top view of a partially assembled eCig 612, consistent with various aspects of the present disclosure. The partial assembly includes a battery 618 and a flex circuit 621 at least partially contained within circumferential light guide 616. The flex circuit being further positioned with an circuit board receiving slot 352 (as shown in FIG. 3A) of the light guide 616, and thereby directing side-fire LEDs $620_{A-D}$ toward opposing distal ends of the circumferential light guide 616. The light, after entering the opposing distal ends of the circumferential light guide 616, travels through the circumferential light guide and is diffused from an outer surface 350 of the light guide 616 based on the illumination pattern of the LED and the variable texturing applied to the outer surface 350. In embodiments where a consistent illumination along a length and circumference of the light guide is desirable, the illumination pattern of the LED in conjunction with the texturing applied to the outer surface 350 of the light guide 616 results in the light guide evenly disbursing light around the circumference of the outer surface 350. In yet other embodiments, it may be desirable to achieve uneven illumination of the light pipe or to create patterns, images, shapes, etc. with the light. In such embodiments, based at least in part on the illumination intensity profile, the surface texturing on the outer surface 350 of the light guide 616 may be varied in such a way as to create such patterns, images, shapes, etc.—by increasing intensity of light distribution at a given location by increasing surface texture, and decreasing intensity of light distribution at a given location by decreasing surface texture.

Wire leads $642_{A-C}$ are communicatively coupled (e.g., soldered) to solder pads on both the flex circuit 621 and controller circuitry 222 (as shown in FIG. 2), thereby facilitating the transmission of power and communication signals between the controller circuitry and flex circuit 621.

A tip diffuser 446 is positioned within a circumference of circumferential light guide 616, and between a flex circuit 612 and an end cap feature 367. The tip diffuser 446 diffusing light received from a light source on the flex circuit 612 and diffuses it on to a distal outer surface 351 of the circumferential light guide 616.

Figure 6B:
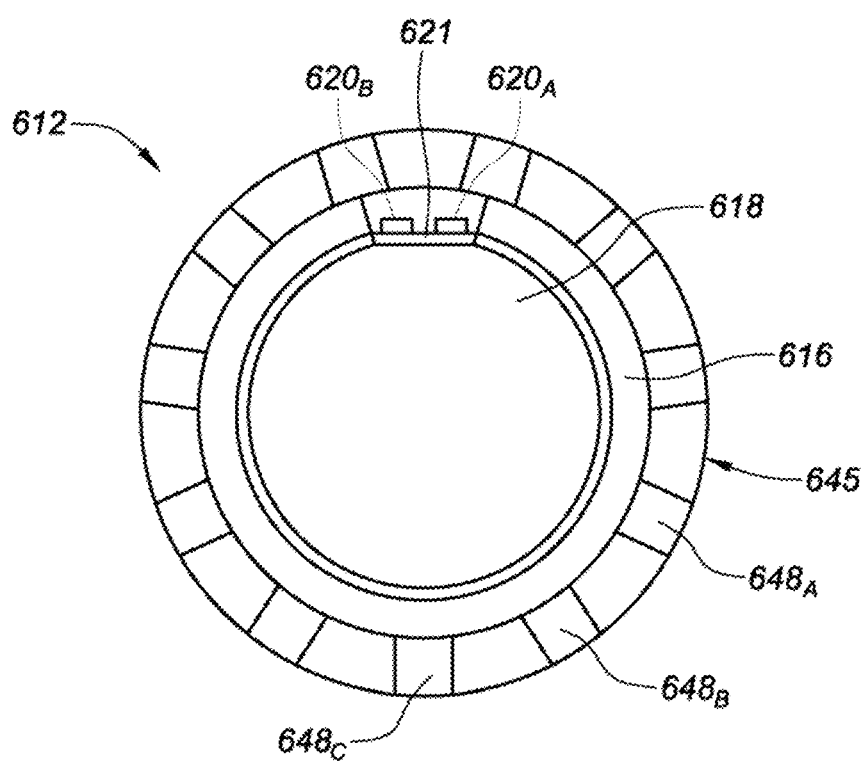
FIG. 6B is an cross-sectional view of the partially assembled eCig taken along line B-B of FIG. 6A, consistent with various aspects of the present disclosure.

FIG. 6B is a cross-sectional front view of the partially assembled power supply portion 612 of FIG. 6A, consistent with various aspects of the present disclosure. As shown in FIG. 6B, LEDs $620_{A-B}$ on flex circuit 621 are positioned in the power supply portion 612 between distal ends of a circumferential light guide 616. When activated, the LEDs $620_{A-B}$ direct light into the distal ends of the circumferential light guide 616 and the light guide evenly diffuses the light from the light guide out of an outer surface 350 thereof. A tube 645 around an outer perimeter of the power supply portion 612 may include translucent portions $648_{A-C}$ (e.g., etch patterns) that allow for the diffused light to escape the power supply portion 612 at specific locations and provide a desired effect. For example, appearing to glow in response to a draw from the user.

Embodiments of the present disclosure are directed to an electronic cigarette including a sensor, controller circuitry, and a light source. The sensor determining a user draw characteristic, and transmitting a draw signal indicative of the determined user draw characteristic. The controller circuitry communicatively coupled to the sensor, and receives the draw signal from which it determines a light intensity signal transmission. The light source is communicatively coupled to the controller circuitry, and receives the light intensity signal from the sensor—thereafter emitting an intensity of light corresponding to the received light intensity signal. In some embodiments, the user draw characteristic comprises a magnitude of a user draw on the electronic cigarette. In more specific embodiments, the sensor comprises a mass airflow sensor, wherein the user draw characteristic corresponds to a mass of air moving through the electronic cigarette during the user draw.

Various embodiments of the present disclosure are directed to an electronic cigarette including a sensor, a light source, and controller circuitry. The sensor determines a magnitude of a draw characteristic, and transmits a signal indicative of the determined magnitude of the draw characteristic. The light source emits a varying intensity of light in response to an input signal. The controller circuitry is communicatively coupled to the sensor and the light source, and the controller circuitry receives, from the sensor, the signal indicative of the determined magnitude of the draw characteristic, associates the determined magnitude of the draw characteristic with a light intensity of the light source, and generates and transmits the input signal to the light source based on the light intensity associated with the determined magnitude of the draw characteristic. In some embodiments, the sensor is a mass airflow sensor that determines a mass flowrate of the draw, a heater coil temperature sensor, or a capacitive velocity sensor.

In various embodiments the association between the determined magnitude of the draw characteristic and the light intensity of the light source are non-linear. In one specific embodiment, the association is a logarithmic transfer function.

A light source as disclosed herein may be one or more light emitting diodes, the one or more light emitting diodes may be dependently and/or independently addressable by the controller circuitry.

In accordance with various aspects of the present disclosure, in response to a change in a draw characteristic measured by a sensor over time, controller circuitry in the eCig may vary the input signal and thereby visually indicate a change in a draw characteristic.

Some embodiments of the present disclosure are directed to a circumferential light guide apparatus including a partial circumferential feature, opposing distal ends on either side of the partial circumferential feature, an aperture between the distal ends, and an outer surface. The opposing distal ends receive and direct light into the partial circumferential feature. In response to receiving light, the outer surface which includes variable surface texture, evenly distributes the directed light along the outer surface of the circumferential light guide. In some embodiments, the circumferential light guide apparatus further includes an electronic circuit board positioned within the aperture. The electronic circuit board including at least one light source substantially directed toward at least one of the opposing distal ends.

Various embodiments of a circumferential light guide apparatus include a tip diffuser coupled to an inner surface of a partial circumferential feature. The tip diffuser receives light directed along a longitudinal axis relative to the partial circumferential feature at a proximal surface of the tip diffuser, and evenly distributes the received light along a distal surface of the tip diffuser. In some aspects of the present disclosure, the tip diffuser is a bi-convex lens with a plurality of diffusing features extending into the proximal surface of the tip diffuser. In specific embodiments, the plurality of diffusing features are pyramidal apertures extending into the proximal surface of the tip diffuser.

Aspects of the circumferential light guide apparatus may include variable surface texture of an outer surface of a partial circumferential feature. In one embodiment, the variable surface texturing being minimal near the opposing distal ends, and increasing with a circumferential distance from the distal ends of the partial circumferential feature.

A circumferential light guide apparatus may also include an electronic circuit board, positioned within the aperture. The electronic circuit board including at least one light source substantially directed toward at least one of the opposing distal ends, and at least one light source substantially directed toward a tip diffuser. In more specific embodiments, the light sources directed substantially toward at least one of the opposing distal ends may be offset relative to one another along a longitudinal axis of the partial circumferential feature.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

| LIST OF REFERENCE SIGNS | |
|---|---|
| 10 | electronic smoking device |
| 12 | end cap |
| 14 | power supply portion |
| 16 | atomizer/liquid reservoir portion |
| 18 | light emitting diode (LED) |
| 20 | air inlets |
| 22 | battery |
| 24 | control electronics |
| 26 | airflow sensor |
| 28 | atomizer |
| 30 | heating coil |
| 32 | wick |
| 34 | central passage |
| 36 | liquid reservoir |
| 38 | air inhalation port |
| 212 | power supply portion |
| 216 | circumferential light guide |
| 218 | battery |
| 220 | LED |
| 221 | flexible printed circuit |
| 222 | controller circuitry |
| 224 | sensor |
| 240 | sub-assembly top |
| 241 | sub-assembly bottom |
| 242 | wire leads |
| 245 | tube |
| 246 | tip diffuser |
| 248 | translucent portion |
| 316 | circumferential light guide |
| 350 | outer surface |
| 351 | distal outer surface |
| 352 | circuit board receiving slot |
| 356 | light texturing |
| 357 | intermediate texturing |
| 358 | heavy texturing |
| 360 | friction rib |
| 361 | partial circumferential feature |
| 362 | retention tooth |
| 363 | longitudinally-extending slot wall |
| 364 | circumferentially-extending slot wall |
| 365 | alignment groove |
| 366 | air inlet channel |
| 367 | end cap feature |
| 368 | light guide positioning ring |
| 446 | tip diffuser |
| 447 | convex lens |
| 448 | light diffusing features |
| 449 | fixation prong |
| 520 | LED |
| 521 | flexible printed circuit |
| 542 | wire leads |
| 555 | right-angled portion |
| 612 | power supply portion |
| 616 | circumferential light guide |
| 618 | battery |
| 620 | LED |
| 621 | flexible printed circuit |
| 642 | wire leads |
| 645 | tube |
| 648 | translucent portion |

What is claimed is:

1. An electronic cigarette comprising:
 a tip diffuser including a bi-convex lens.

2. The electronic cigarette of claim 1, wherein the tip diffuser is positioned at a distal tip of the electronic cigarette.

3. The electronic cigarette of claim 1, wherein the bi-convex lens includes side-walls configured and arranged to further facilitate diffusion of light through the tip diffuser.

4. The electronic cigarette of claim 1, wherein a distal surface of the bi-convex lens is configured and arranged to distribute light received at a proximal surface across a wide viewing angle.

5. The electronic cigarette of claim 2, wherein the tip diffuser is configured and arranged to
 receive light directed along a longitudinal axis of the electronic cigarette at a proximal surface of the tip diffuser, and
 evenly distribute the received light along a distal surface of the tip diffuser.

6. The electronic cigarette of claim 3, wherein the side-walls are selected from the group consisting of: sloped, straight, or rounded.

7. The electronic cigarette of claim 2, wherein the tip diffuser is configured and arranged to diffuse light received from a single point source on a proximal surface of the tip diffuser and to produce even illumination along a distal surface of the tip diffuser.

8. An electronic cigarette comprising:
 a tip diffuser including a plurality of light diffusing features extending into a proximal surface of the tip diffuser.

9. The electronic cigarette of claim 8, wherein the plurality of light diffusing features are pyramidal apertures.

10. The electronic cigarette of claim 8, wherein the plurality of light diffusing features are evenly distributed across the proximal surface of the tip diffuser.

11. The electronic cigarette of claim 5, further including an electronic circuit board positioned proximal to the tip diffuser, the electronic circuit board comprising at least one light source directed toward the tip diffuser.

12. The electronic cigarette of claim 8, wherein the plurality of light diffusing features are unevenly distributed across the proximal surface of the tip diffuser.

13. The electronic cigarette of claim 8, wherein the plurality of light diffusing features form a visible pattern on a distal surface of the tip diffuser.

14. The electronic cigarette of claim 8, wherein the tip diffuser further includes secondary light diffusing features selected from the group consisting of: surface texturing, and material characteristics or additives to the tip diffuser that facilitate internal light diffusion.

15. The electronic cigarette of claim 8, further including a second plurality of light diffusing features extending into a distal surface of the tip diffuser.

* * * * *